United States Patent [19]

Fukuda et al.

[11] Patent Number: 4,474,051

[45] Date of Patent: Oct. 2, 1984

[54] METHOD FOR MEASURING THE CONCENTRATION OF A COMBUSTIBLE COMPONENT

[75] Inventors: Hideki Fukuda; Hisashi Morikawa, both of Hyogo, Japan; Hideki Nakatani, deceased, late of Osaka, Japan, by Tohru Nakatani, legal representative

[73] Assignee: Kanegafuchi Kagaku Kogyo Kabushiki Kaisha, Osaka, Japan

[21] Appl. No.: 475,938

[22] Filed: Mar. 16, 1983

[30] Foreign Application Priority Data

Mar. 16, 1982 [JP] Japan .................................. 57-42469

[51] Int. Cl.³ ............................................. G01N 27/12
[52] U.S. Cl. ............................................. 73/19; 73/23
[58] Field of Search ........................ 73/19, 23, 27 R; 340/634; 324/71.5; 422/98

[56] References Cited

U.S. PATENT DOCUMENTS 4,257,257  3/1981  Dairaku et al. ........................ 73/19
4,404,284  9/1983  Heider et al. .......................... 73/19

Primary Examiner—Stephen A. Kreitman
Attorney, Agent, or Firm—Sughrue, Mion, Zinn, Macpeak & Seas

[57] ABSTRACT

A method of measuring a combustible component in a liquid or gas employs a gas having a high oxygen content, instead of air or an inert gas, as the carrier gas to thereby improve drastically the scope and accuracy of measurement by a semicondutor gas sensor. The carrier gas having a high oxygen content is supplied into a combustible component sampler formed from a gas-permeable membrane and disposed in the liquid or gas to be tested so that the combustible component may be diffused into the carrier gas through the gas-permeable membrane. The carrier gas entraining the combustible component therein is introduced into a detector having a semiconductor gas sensor, in which the combustible component is detected, and its concentration is determined continuously or intermittently.

6 Claims, 6 Drawing Figures

METHOD FOR MEASURING THE CONCENTRATION OF A COMBUSTIBLE COMPONENT

BACKGROUND OF THE INVENTION

1. Field of the Invention

This invention relates to a method of measuring quickly and accurately the concentration of a combustible component in a liquid or gas phase. More particularly, it is concerned with a method of measuring the concentration of a combustible component accurately in which a gas having a high oxygen content is used as a carrier gas for detection by a semiconductor gas sensor.

2. Description of the Prior Art

A flame ionization detector, a catalyst type detector, a semiconductor gas sensor, etc. are known for use in the measurement of a combustible component. The flame ionization detector is, however, large and expensive, though it is accurate. As it uses hydrogen gas, it presents a great problem in safety when it is used in a chemical plant, and involves difficulty in portable application. The catalyst type detector is small and inexpensive, but its sensitivity is greatly lowered if the catalyst is poisoned by a certain substance, such as chloride or thionide. It has a relatively short life due to oxidation upon exposure to a high temperature, or deterioration by a hot combustible gas. The semiconductor gas sensor is inexpensive and free from any substantial deterioration when an inert gas such as nitrogen or helium, or air is used as a carrier gas. It is, however, useful for measuring only a limited concentration of a combustible component, and low in accuracy. Thus, the known detectors have various drawbacks which hinder their industrial application.

SUMMARY OF THE INVENTION

The inventors of this invention have thought of using the semiconductor gas sensor and made an extensive study to remove its drawbacks. As a result, they have found it possible to achieve a wider scope of measurement and a higher degree of accuracy if a gas having a high oxygen content or pure oxygen is used as the carrier gas.

According to this invention, there is, thus, provided a method for the measurement of a combustible component in a liquid or gas phase, which comprises mixing the combustible component in gaseous form with a carrier gas containing at least about 50% by volume of oxygen, and then introducing said carrier gas into a detector including a semiconductor gas sensor, whereby said combustible component is detected, and its concentration is measured continuously or intermittently.

DESCRIPTION OF THE PREFERRED EMBODIMENTS

Figure 1:
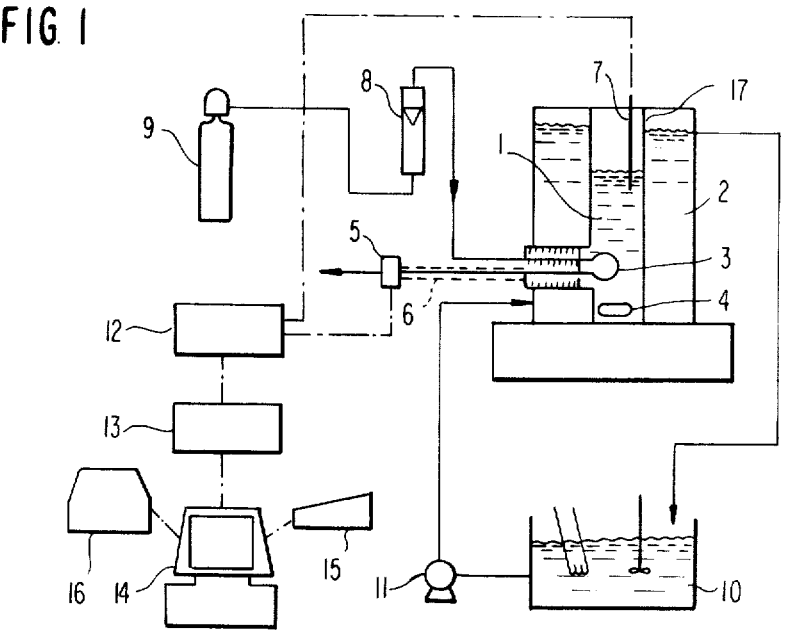
FIG. 1 is a flow diagram illustrating by way of example the application of the method according to this invention.

The method of this invention will now be described in further detail with reference to the drawings, though it is not limited to what is shown in the drawings, or what will hereinafter be described with reference thereto.

Referring first to FIG. 1, there is shown a flow diagram in which the method of this invention is used by way of example for measuring the concentration of ethanol in a liquid. A measuring tank 17 holds the liquid 1 containing ethanol. A combustible component sampler 3 is immersed in the liquid 1, and comprises a tube formed from a porous, gas-permeable tetrafluoroethylene membrane. The tank 17 is provided with a jacket 2, and the liquid 1 is maintained at a constant temperature by a temperature control medium which is circulated by a pump 11 from a constant temperature tank 10 into the jacket 2. The tank 17 is also provided with a stirrer 4 for mixing the liquid 1 uniformly, and a thermometer 7. A carrier gas composed of pure oxygen is supplied continuously at a predetermined rate from a gas cylinder 9 into the sampler 3 through a flow meter 8. The ethanol which the liquid 1 contains is diffused in gaseous form into the carrier gas through the pores in the porous wall of the sampler tube. The carrier gas thus containing ethanol is directly introduced into a semiconductor gas sensor 5. An electric signal generated with sensor 5 is transmitted to a microcomputer 14 through an amplifier 12 and A/D converter 13, and the microcomputer 14 calculates the concentration of ethanol in accordance with a predetermined formula for calculation. A printer 15 and a floppy disk 16 are connected to the microcomputer 14.

As the semiconductor gas sensor is a sensor of which the resistance is variable with the concentration of the combustible component in the carrier gas, it is also possible to employ a voltmeter or like means which enables the direct reading of an electric signal from the amplifier 12, i.e., a voltage change, instead of using the A/D converter 13 and the microcomputer 14 as hereinabove described.

Figure 2:
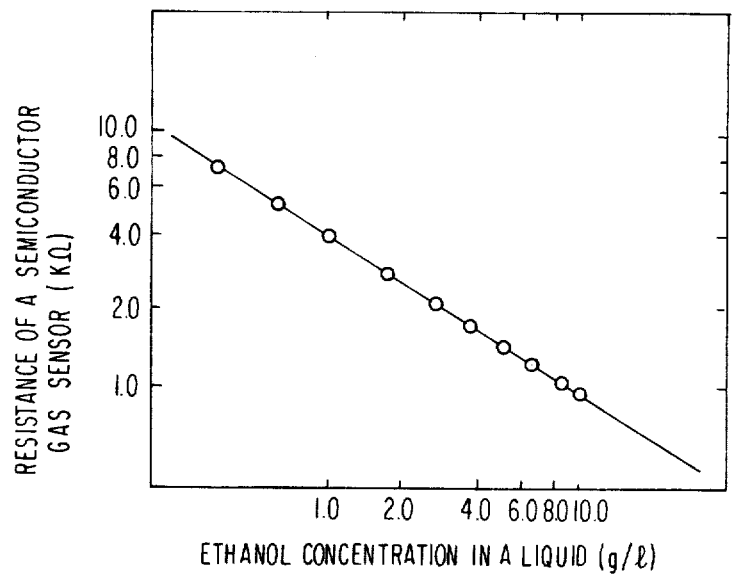
FIG. 2 is a graph showing the relation between the ethanol concentration in a liquid and the resistance of a semiconductor gas sensor.

FIG. 2 is a graph showing by way of example the relation between the concentration of ethanol in water and the resistance of a sensor formed from a commercially available sintered n-type semiconductor composed mainly of $SnO_2$. The results shown in FIG. 2 are of the measurement conducted under the following conditions:

Semiconductor sensor: TGS #812 (trademark of FIGALO GIKEN K.K.);
Liquid temperature: 32° C.;
Porous teflon tube: FLUOROPORE (trademark of SUMITOMO ELECTRIC INDUSTRIAL CO., LTD.) having a length of 10 cm, an inside diameter of 3 mm, a pore diameter of 0.45 micron and a porosity of about 50%;
Carrier gas: Pure oxygen having a purity of at least about 99%;
Gas flow rate: 60 ml/min.

As is obvious from FIG. 2, the resistance and the concentration of ethanol show a linear relation on logarithmically ruled graph paper, and are closely correlated to each other as represented by the following formula, so that the concentration of ethanol can be calculated accurately if the resistance of the sensor is measured:

$$R_S = \beta C_E^{-\alpha} \quad (1)$$

where $R_S$: Resistance of the sensor (kΩ),
$C_E$: Concentration of ethanol in a liquid (g/liter);
$\alpha, \beta$: Constants of which the values depend on the conditions prevailing in the system.

The value obtained from equation (1), however, varies considerably with the concentration of oxygen in the carrier gas. This is particularly true in the event air, which contains about 21% of oxygen, is used as the carrier gas. The value of $\alpha$ in equation (1) is so small that the resistance shows only a very small change as compared with the change in the concentration of ethanol. This makes it difficult to detect variation of an electric signal accurately. Various gaseous mixtures having different oxygen contents have, therefore, been tested for use as the carrier gas. As a result, it has been found that an increase in the concentration of oxygen in the carrier gas brings about an increase in the resistance of the sensor, and that a very high accuracy of measurement can be obtained when a gas containing at least about 50% by volume of oxygen, or preferably, ozygen gas having a purity of at least about 99% by volume is used as the carrier gas.

The porous tetrafluoroethylene tube which has an inside diameter of 2 to 10 mm is preferably used. The carrier gas is preferably supplied at a superficial velocity (gas flow rate/inside cross-sectional area of tube) in the range of about 4 to about 50 cm/sec. Any deviation from this range may result in a reduction in the accuracy of the resistance value obtained. The tube may have a length which enables the realization of an equilibrium between the concentration of the combustible component in the carrier gas at the outlet of the tube and the concentration of the combustible component in the liquid or gas phase to be measured. When the tube is made of porous tetrafluoroethylene, its appropriate length may be in the range of, say, 2 to 20 cm.

Although porous tetrafluoroethylene is excellent for the mass transfer as hereinabove described, it is also possible to use a tube formed from any other material that is permeable to a combustible component, for example, a silicone, polypropylene or polyester resin, or a vinyl halide resin such as polyvinyl chloride. The use of any such tube does not always bring about any change in the aforesaid range of the flow rate for the carrier gas. As regards the tube length, it is easy to obtain experimentally the length which provides the aforesaid equilibrium.

If the carrier gas saturated with combustible gas and water vapor is cooled to a temperature lower than that of the liquid to be tested when it is discharged from the tube through the sensor, a part of the water vapor may be condensed into liquid drops. It is also probable that the combustible component to be assayed may be condensed, or dissolved in the liquid drops, resulting in an inaccurate measurement. If those liquid drops enter the detector, they impair the reliability or stability of measurement, and do damage to the sensor. In order to prevent such condensation, it is necessary to ensure that the passage for the carrier gas between the outlet of the tube and the outlet of the detector be, as a whole, maintained at a temperature which is at least equal to that of the liquid to be tested. In this connection, it is practically effective to provide a heater for the carrier gas passage as shown at 6 in FIG. 1. The heater may be of any customary type, and may, for example, comprise a double-walled tube having an outer tube through which warm water is passed, while its inner tube defines the carrier gas passage. Alternatively, it may, for example, comprise one or more warm water tubes wound about the carrier gas passage, or a nichrome wire wound about the carrier gas passage. It is desirable to surround the heater by a heat-insulating material, or an epoxy, vinyl chloride, propylene, styrene, or other high molecular resin coating or molding.

It is also advisable to surround the sensor by a warm water tube, or an electric heater such as a nichrome wire, and put a heat-insulating material around any such heater. The temperature and quantity of such warm water or the voltage applied to the nichrome wire may be so controlled as to maintain the sensor at a constant temperature.

The method of this invention may be used for both continuous and intermittent measurements. The combustible components which can be measured by the method of this invention include volatile combustible substances, such as hydrocarbons, alcohols, esters, ethers, aldehydes, organic acids and mercaptans, and lower hydrocarbons and other substances which are gaseous at ordinary room temperature. More specifically, the method of this application is applicable to ethanol, methanol, acetone, ethyl ether, ethyl acetate, methyl ether, ethylene, ethane, acetylene, vinyl chloride or other synthetic resin monomer gas, propane gas, natural gas, town gas, gasoline, carbon monoxide, ammonia gas, and any other substance that can be measured by a semiconductor gas sensor.

For the method of this invention, it is possible to use any of the commercially available semiconductor gas sensors known under the names of TGS#812, TGS#813 and TGS#109 (trademarks of FIGALO GIKEN K.K.). They are formed from a sintered n-type semiconductor consisting mainly of $SnO_2$. It is, however, possible to use any other sensor, too. The method of this invention enables a very wide scope of measurement with a high degree of accuracy as compared with any conventional method employing air as the carrier gas.

Figure 3:
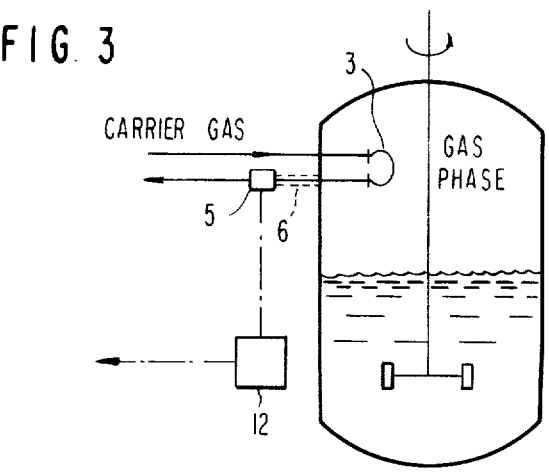
FIGS. 3 to 5 are diagrams showing by way of example the application of this invention for the measurement of a combustible component in a gas phase.
Figure 4:
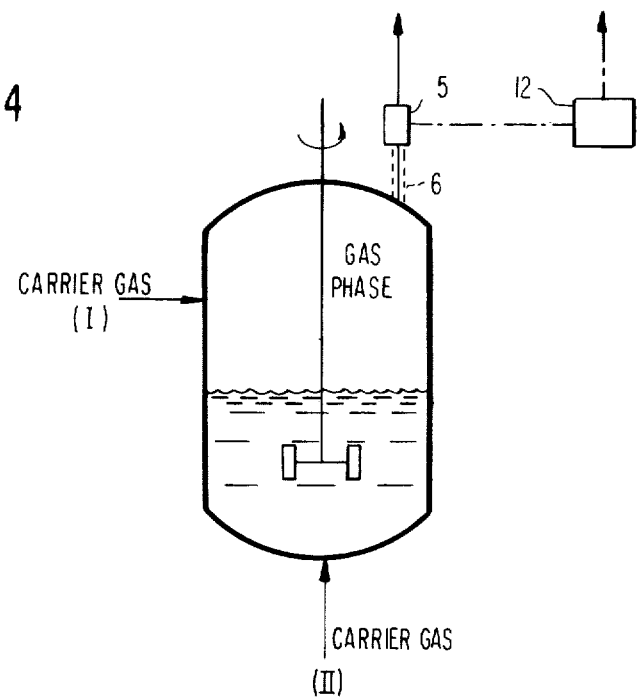
Figure 5:
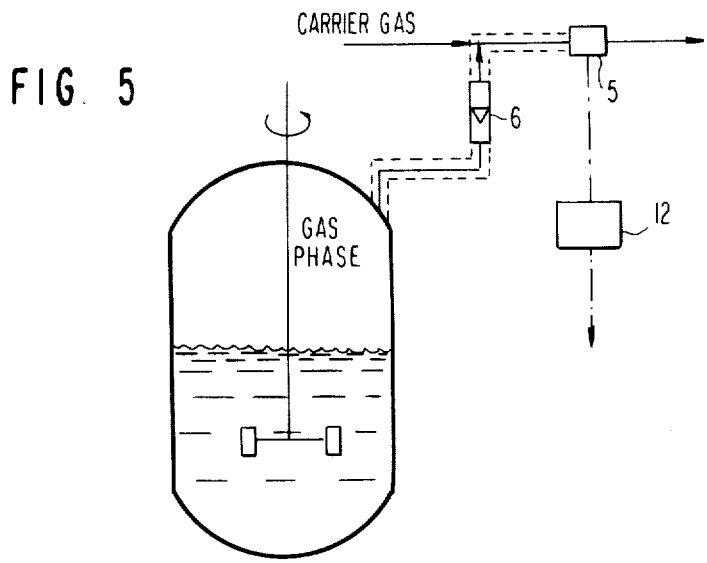

Although FIG. 1 shows an arrangement for measuring the concentration of ethanol in a liquid, the method of this invention is, of course, applicable to the measurement of a combustible substance in a gas phase, too. FIGS. 3 to 5 show by way of example the arrangements for measuring the concentration of a combustible substance in a gas phase. The arrangement shown in FIG. 3 employs a porous tetrafluoroethylene tube, while no such tube is used in the arrangement shown in FIG. 4 or 5.

The arrangement shown in FIG. 4 is applicable to the case in which a combustible substance is present only in a small quantity as, for example, in a baker's yeast fermenter, and the gas containing the combustible substance in the fermenter is directly supplied to the gas sensor 5. The carrier gas may be blown into the gas phase (I) or the liquid phase (II), and in the latter case, it is usually possible to determine the combustible substance in the liquid phase.

According to the arrangement shown in FIG. 5, a certain quantity of gas is taken constantly or intermittently from the gas to be tested, and mixed with a certain proportion of the carrier gas, and the resulting gaseous mixture is introduced into the gas sensor 5.

As is obvious from the foregoing description, the method of this invention employs a gas having a high oxygen content, instead of air or an inert gas, as the carrier gas to improve drastically the scope and accuracy of measurement by a semiconductor gas sensor. Therefore, the method of this invention is superior to any conventional method or arrangement for similar measurement economically, operationally and in accuracy, and of great advantage in industrial application.

The invention will now be described in further detail with reference to several examples which do not limit the scope of this invention.

EXAMPLES 1 AND 2, AND COMPARATIVE EXAMPLES 1 TO 3

The apparatus shown in FIG. 1 was used for the anaerobic fermentation of a baker's yeast (*Saccharomyces cerevisiae*) in the tank 17. The concentration of the ethanol thereby produced was measured by the method of this invention, and also by gas chromatography for comparison purposes. Pure oxygen having a purity of about 99.8% or above was used as the carrier gas in EXAMPLE 1, and a gas containing about 50% of oxygen in EXAMPLE 2. The other test conditions were as follows:

Conditions for fermentation: 32° C., pH 4.5, with a cell concentration of 10 to 15 g/liter.

Medium composition (per liter): 2,500 mg phosphoric acid, 2,000 mg potassium chloride, 2,000 mg magnesium sulfate, 500 mg ammonium sulfate, 100 mg sodium chloride, 100 mg calcium chloride, 100 mg $FeSO_4$, 100 mg $ZnSO_4$, 20 mg $MnSO_4$, 5 mg $CuSO_4$, 0.1 mg biotin, 20 mg vitamin $B_1$, 1 mg vitamin $B_6$, 20 mg calcium pantothenate, 100 mg inositol, 1 mg nicotinic acid, 0.02 mg folic acid and 1,000 mg yeast extract.

Conditions for measurement:
Semiconductor sensor: TGS#812 (trademark of FIGALO GIKEN K.K.);
Carrier gas: 60 ml/min.;
Sampler: Porous tetrafluoroethylene tube FLUOROPORE (trademark) having a length of 10 cm, an inside diameter of 3 mm and a pore diameter of 0.45 micron.

For comparison purposes, air (having an oxygen content of 21%) was used as the carrier gas in COMPARATIVE EXAMPLE 1, a gas containing about 40% of oxygen in COMPARATIVE EXAMPLE 2, and nitrogen gas in COMPARATIVE EXAMPLE 3. All the other conditions of the COMPARATIVE EXAMPLES duplicated those of the EXAMPLES of this invention. The results are shown in FIG. 6.

Figure 6:
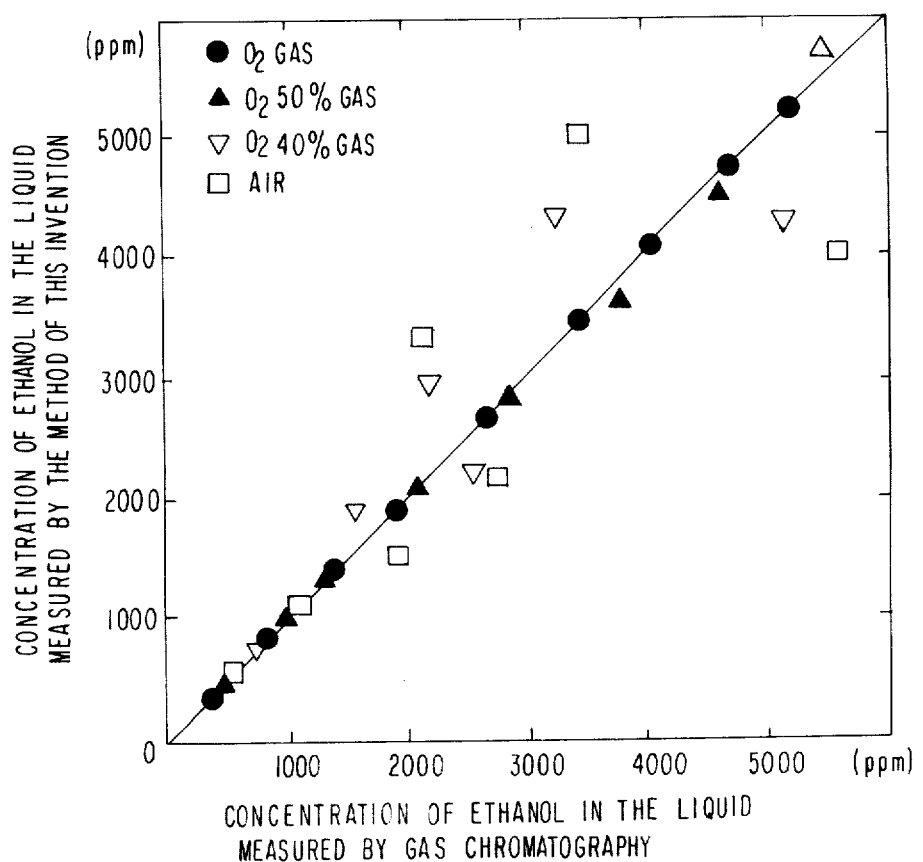
FIG. 6 shows the results of measurement obtained in the examples of this invention and the comparative examples.

In FIG. 6, the abscissa indicates the concentration of ethanol in the liquid as measured by the method of this invention, while the ordinate shows the concentration of ethanol as measured by gas chromatography. As is obvious from FIG. 6, the results of EXAMPLES 1 and 2 employing pure oxygen and a gas containing about 50% of oxygen, respectively, as the carrier gas showed good coincidence with those obtained by gas chromatography. The results of COMPARATIVE EXAMPLES 1 and 2 employing air and a gas containing about 40% of oxygen, respectively, as the carrier gas, which are shown by a square and a triangular mark, respectively, showed a difference of about 20% or more at a concentration of about 2,000 ppm or more from those obtained by gas chromatography. This was due to a greater error in the detection of a change occurring to the resistance of the sensor as a result of a change in the concentration of ethanol, since the value of $\alpha$ in equation (1) decreases with a reduction in the concentration of oxygen in the carrier gas. In COMPARATIVE EXAMPLE 3 employing nitrogen as the carrier gas, it was impossible to determine the concentration of ethanol, since the sensor did not show any appreciable change in resistance despite the change in the concentration of ethanol.

The results hereinabove described testify that the method of this invention enables the measurement of a combustible substance with a very high degree of accuracy.

What we claim is:

1. A method for measuring the concentration of a combustible component in a liquid or gas phase comprises the steps of:
    mixing a combustible component in a liquid or gas phase with a carrier gas containing at least 50% of oxygen in gaseous form, and
    introducing said carrier gas into a detector having a semiconductor gas sensor, whereby said component is detected, and its concentration is determined continuously or intermittently.

2. The method of claim 1, wherein said carrier gas contains at least 99% of oxygen.

3. The method of claim 1, wherein said carrier gas is supplied into a combustible component sampler formed from a gas-permeable membrane and disposed in said liquid or gas phase to entrain said combustible component diffused therinto through said membrane, before said carrier gas is introduced into said detector.

4. The method of claim 3, wherein said sampler comprises a porous tetrafluoroethylene tube.

5. The method of claim 3, wherein said carrier gas is supplied into said sampler at a superficial velocity of 4 to 50 cm/sec.

6. The method of claim 1, wherein said sensor is made of a semiconductor consisting mainly of $SnO_2$.

* * * * *